US009585621B2

(12) United States Patent
Mitov

(10) Patent No.: US 9,585,621 B2
(45) Date of Patent: Mar. 7, 2017

(54) TECHNIQUE FOR REAL-TIME REMOVAL OF POWER LINE INTERFERENCE IN ECG

(71) Applicant: Iliya Mitov, Vidin (BG)

(72) Inventor: Iliya Mitov, Vidin (BG)

( * ) Notice: Subject to any disclaimer, the term of this patent is extended or adjusted under 35 U.S.C. 154(b) by 1018 days.

(21) Appl. No.: 13/849,666

(22) Filed: Mar. 25, 2013

(65) Prior Publication Data

US 2014/0288845 A1 Sep. 25, 2014

(51) Int. Cl.
A61B 5/0402 (2006.01)
A61B 5/00 (2006.01)

(52) U.S. Cl.
CPC .......... *A61B 5/7203* (2013.01); *A61B 5/0402* (2013.01)

(58) Field of Classification Search
USPC .......................................... 702/191; 600/509
See application file for complete search history.

(56) References Cited

U.S. PATENT DOCUMENTS

| | | | |
|---|---|---|---|
| 4,537,200 A * | 8/1985 | Widrow | ............... A61B 5/0424 600/509 |
| 5,687,735 A | 11/1997 | Forbes et al. | |
| 6,216,031 B1 | 4/2001 | Findeis et al. | |
| 6,351,664 B1 | 2/2002 | Brodnick | |
| 7,286,983 B2 | 10/2007 | Li et al. | |
| 7,894,885 B2 | 2/2011 | Bartal et al. | |
| 2012/0157865 A1 * | 6/2012 | Stein | ................... A61B 5/04014 600/509 |
| 2014/0121548 A1 * | 5/2014 | Lou | .................... H03H 21/0021 600/509 |

OTHER PUBLICATIONS

I. P. Mitv, "A method for reduction of power line interference in the ECG", Medical Engineering & Physics, Dec. 2004, pp. 879-887, vol. 26, No. 10, Institute of Physics and Engineering in Medicine, published by Elsevier.

* cited by examiner

Primary Examiner — Mohamed Charioui
(74) Attorney, Agent, or Firm — Michael Coblenz

(57) ABSTRACT

A technique for real-time removal of power line interference (PLI) in electrocardiograms (ECG) with sampling rate a relevant integer multiple of the nominal power line frequency (NPLF), comprising band-pass PLI filtering of the ECG, determining expedient weights and weighted Least-Squares parabolic approximating downsampled to the NPLF series of band-pass PLI filtered values. The disclosed technique utilizes only integer arithmetic, includes pre-adjusting for the routine ECG sampling rates, causes negligible ringing and is still accurate in the common occurrences of PLI with deviating from the nominal 60 or 50 Hz frequency and varying amplitude.

3 Claims, 6 Drawing Sheets

TECHNIQUE FOR REAL-TIME REMOVAL OF POWER LINE INTERFERENCE IN ECG

CROSS REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to the measurement of electrophysiological signals and in particular to the removal of power line interference in electrocardiograms (ECG).

2. Description of the Related Art

Power line interference (PLI) often damages ECG despite proper grounding, shielding and amplifier design, therefore various digital methods for removing 60 or 50 Hz PLI in ECG are known in the art. Some of these methods use external reference signal to facilitate the PLI removal, but require additional hardware and are impracticable in the battery supplied mobile ECG devices. Many of the methods that process solely the ECG use notch filters that involve noticeable distortions and ringing effect at the QRS-complexes in the ECG, that is why others methods of this group divide the treated ECG into "quiet" and "event" epochs and extrapolate the PLI estimates of a "quiet" to the following "event" epoch. The more accurate of these last methods are quite complex and suited only for offline usage, whereas the simpler ones can be realized in real-time, but their performance considerably worsens in the common occurrences of PLI with deviating from the nominal 60 or 50 Hz frequency and varying amplitude.

Another method was proposed by the author of the disclosed invention in a previously published paper (I. P. Mitov, "A method for reduction of power line interference in the ECG", *Medical Engineering & Physics*, vol. 26, No. 10, December 2004, pp. 879-887). This method is for reduction of 50 Hz PLI in ECG sampled with 250 Hz that fit both the purpose and the ECG spectral range (with equal reason relevant for removing 60 Hz PLI are ECG sampling rates 240, 300 or 360 Hz).

The considered method uses adequate parabolic model of the pure ECG and estimates its inconstant part, that is then subtracted to obtain a residual signal containing PLI, by Least-Squares (LS) solving a system of properly derived equations. Moreover, the squared error of another such system is utilized to determine a weight (that ranges from one in the very "quiet" ECG segments to nearly zero at the large and sharp QRS-complexes) for the subsequent LS approximations.

The residual PLI signal is further subjected to discrete Fourier transform separating the PLI components related to the nominal power line frequency (NPLF) and its harmonics, and the initial estimates of all these PLI components are obtained by apposite averaging.

The separate series of initial PLI estimates are downsampled to the NPLF (thereby due to the "aliasing" phenomenon their frequency content appears near to the spectral origin), LS approximated using third order polynomials and the above-cited weights, and thus obtained final estimates of the PLI components related to the NPLF and its harmonics are subtracted from the corresponding ECG sample.

The considered method is very accurate, even if the PLI is with deviating from 50 Hz frequency and varying amplitude, but its procedures are to a certain extent unduly elaborated and relatively burdensome for real-time implementation in the electrocardiographic (ECG) devices.

BRIEF SUMMARY OF THE INVENTION

The present invention is a new and useful improvement of the above method, whose computational load is substantially reduced but even higher accuracy is achieved.

The disclosed technique for real-time removal of power line interference in ECG comprises the following procedures:

(a) storing the recent samples obtained by analog-to-digital conversion (ADC) of the treated ECG signal in a First-In-First-Out (FIFO) buffer;

(b) filtering the ECG samples by a series of two identical band-pass PLI filters that are based on double moving average and scaled-up to obviate fractional numbers;

(c) determining the error in LS linear approximation of the recent four differences of phased with the NPLF ECG samples and storing in the respective FIFO buffers the last two approximation errors and their sum as new smoothed error;

(d) finding out the maximum of the smoothed errors from 50-56 ms ECG around the current output value of the band-pass PLI filters, computing a ranged from 1 to 1000 integer weight for the final LS approximation and storing this weight and its product with the current PLI filtered value in FIFO buffers of lengths corresponding to 0.4 s;

(e) estimating PLI by weighted LS parabolic approximating the current sub-series of downsampled to the NPLF band-pass PLI filtered values and subtracting thus obtained PLI estimate from the target ECG sample that is last in the respective FIFO buffer.

It can be seen that in contrast to the previous method the disclosed technique instead of separately treats the PLI components related to the NPLF and its harmonics in total and uses a lower polynomial order in the weighted LS approximation. Together with the usage of solely integer arithmetic these properties enable real-time implementation of the disclosed technique that is besides pre-adjusted for removing 60 Hz PLI in ECG sampled with 240, 300 or 360 Hz and for removal of 50 Hz PLI in ECG sampled with 250 or 300 Hz. Owing to its performance the technique is fitted for both single and multi-lead ECG devices with these routine sampling rates, and one skilled in the art can easily adapt the disclosed technique for real-time removal of PLI in research-grade ECG sampled with multiple higher rate using an expedient additional downsampling, e.g. a 1200 Hz ECG to four sub-series of samples with the admissible 300 Hz.

DETAILED DESCRIPTION OF THE INVENTION

Figure 1:
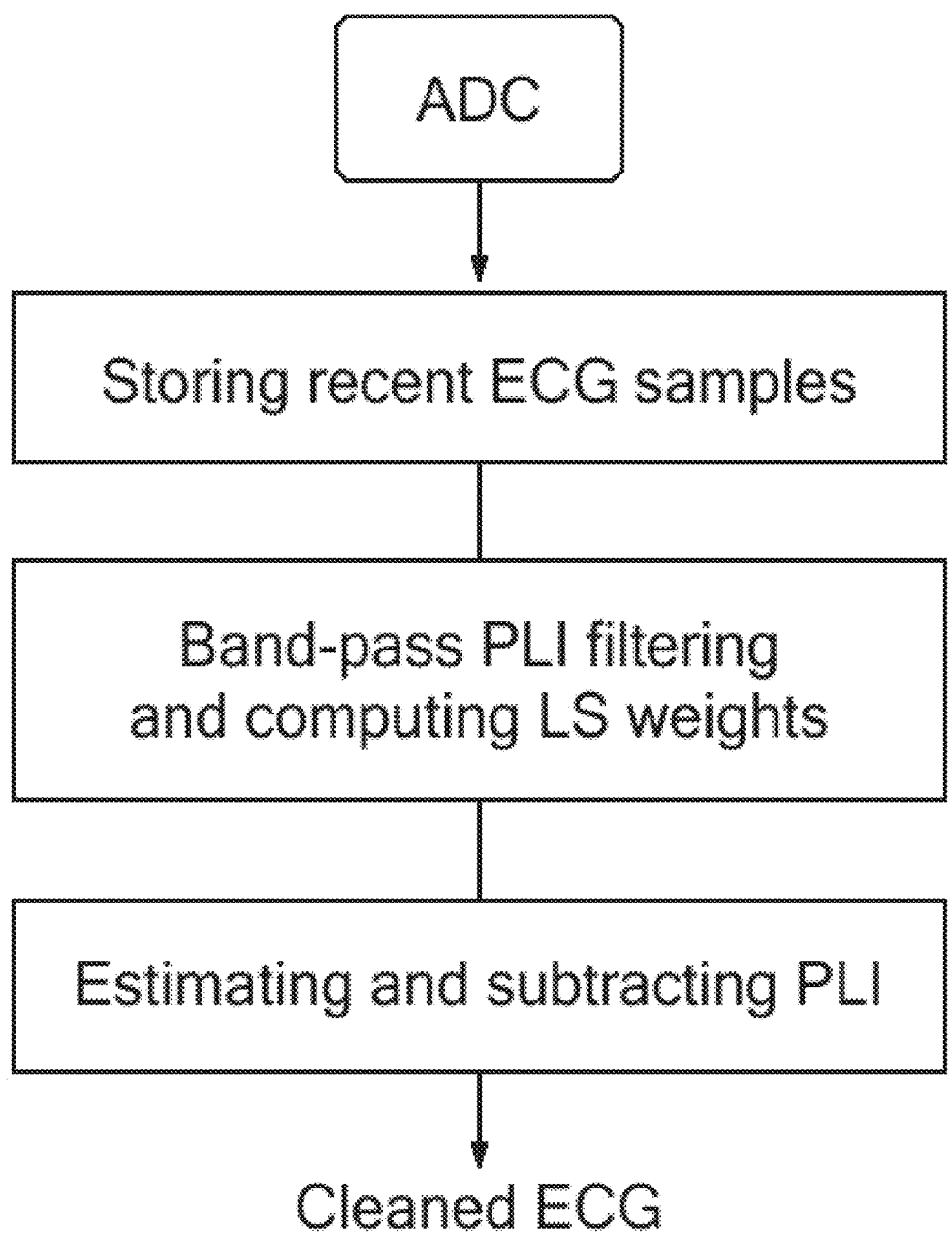
FIG. 1 represents a concise block diagram of the disclosed technique for real-time removal of power line interference in ECG.

To fully elucidate the present invention, that is developed and tested using MATLAB® for MS-Windows®, in addition to the concise block diagram shown in FIG. 1, Table 1 submits the listing of an M-file that is ready for offline usage and includes certain directives for the online implementation of the disclosed technique for real-time removal of PLI in ECG (first such directive of proved reliability is to replace all present floating point 'double' operations on 64-bit data by their much faster 'int64' counterparts). This M-file has four parts that realize the technique pre-adjusting (lines 4-48), memory allocation (lines 50-61), ECG acquisition (lines 63-74) and the processing of each consecutive ECG sample (lines 76-141).

The parameters of the disclosed technique are set according to their interdependences and the imposed general requirements. All case-dependent parameters nf, k, kp, nw and nx for memory allocation have decreased by one mates used to shift the data in the respective FIFO buffers before every new storing. The number nf of smoothed errors and their first index ff ensure that the LS weights rely on all ECG samples in 50-56 ms around the current output value of the band-pass PLI filters. The weighting is finished using the denominator addend da (the only experimentally adjusted parameter explained further) and the associated numerator addend na. The integer ratio k of the selected ECG sampling rate sf and NPLF is utilized to organize the band-pass PLI filters and kp is used to form phased with the NPLF differences. The foremost output value of these filters is produced at the second transitional index i2 and corresponds to the stored ECG sample with index i1 equal to the primary filter length. The number nw of stored LS weights ensures that the final approximation covers 0.4 s (i.e. 2 sf/5 sampling intervals) around the central one of the treated band-pass PLI filtered values. Thus the first PLI estimate is obtained at the third transitional index i3, the target ECG sample that is last in the respective FIFO buffer has the presented index nx and therefore the disclosed technique has real-time delay of about 0.2 s and initial latency a little above 0.4 s. After the downsampling to the NPLF the final LS approximating treats sub-series of 2m+1 weights and band-pass PLI filtered values indexed from −m to m, where the parameter m is equal to 12 for NPLF 60 Hz and to 10 for NPLF 50 Hz.

About the memory allocation it should be added that the modern processors have fast specialized operators for shifting the data in FIFO buffers and that the initial zeroing of the buffers x, d, y, z, and u is requisite for the correct start of the disclosed technique.

The first active step of this technique is the ECG acquisition, that in the online version consists in the ADC sampling shown in FIG. 1, and in the present M-file includes loading of a real ECG record and adding to it a simulated PLI for the trial explained further.

Figure 2:
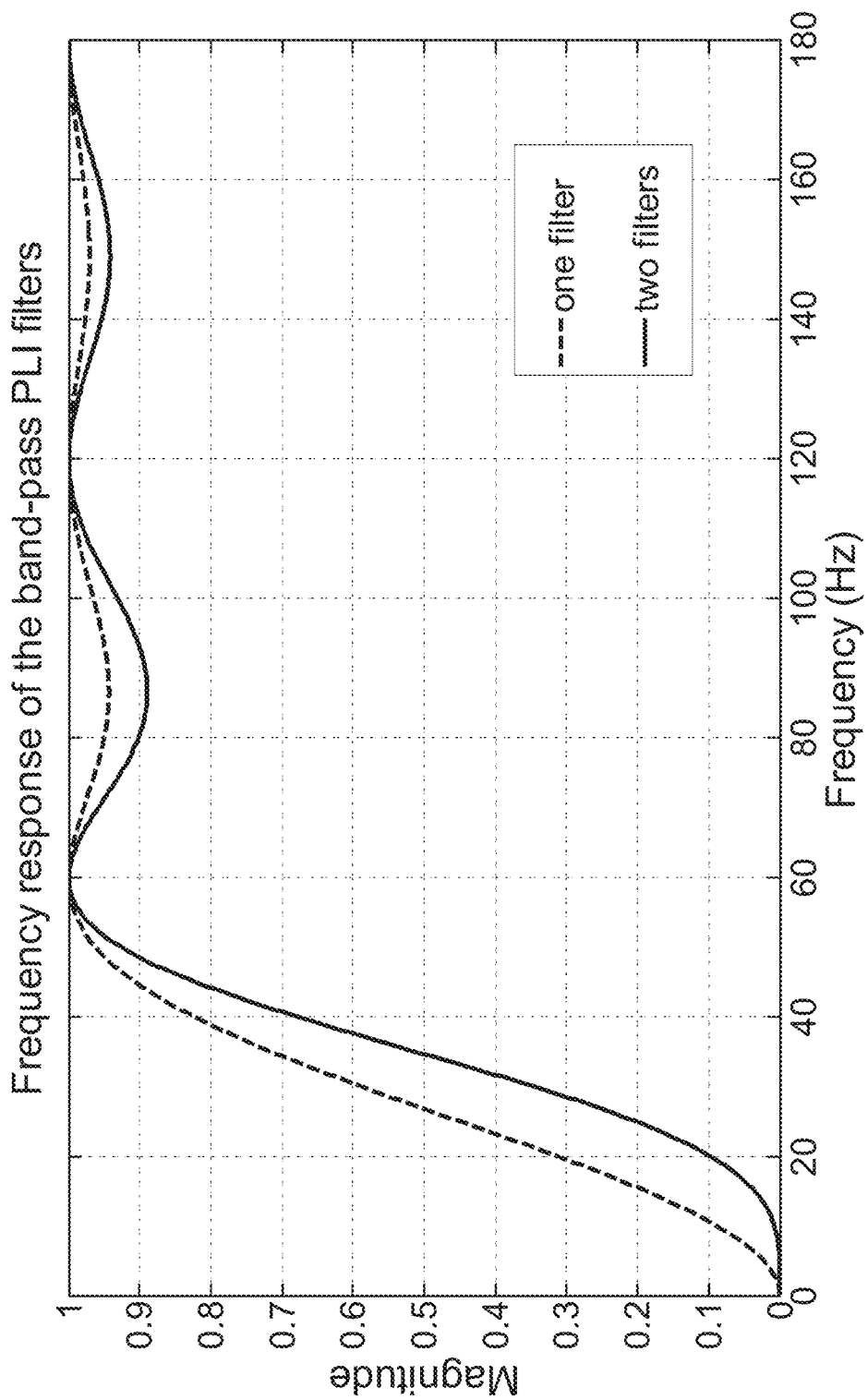
FIG. 2 shows the frequency response of the band-pass PLI filters used by the disclosed technique in the case of NPLF 60 Hz and ECG sampling rate 360 Hz.

After the preparative operations on the running index i that in the online version of the disclosed technique is used only to organize its starting and then detained to prevent eventual overflow in continuously working ECG devices, the processing of each one consecutive ECG sample comprises the procedures that are indicated in FIG. 1 and elucidated below according to lines 81-136 of Table 1:

Storing in the respective FIFO buffers x, d and y the current ECG sample, its phased with the NPLF difference and the current recursive sum of the last k ECG samples (note that every storing is preceded by appropriate shifting, that x, d and y are initially zeroed and that the elements in d and y are of data type 'int32' to prevent arithmetic problems);

Provided that i≤i1, computing and storing in the FIFO buffer z the output value of the primary band-pass PLI filter. Taking into account that $y(1)=x(1)+x(2)+\ldots+x(k-1)+x(k)$, $y(2)=x(2)+x(3)+\ldots+x(k)+x(k+1), \ldots, y(k)=x(k)+x(k+1)+\ldots+x(2k-2)+x(2k-1)$, line 90 of the M-file shows that this filter with impulse response $[-1, -2, \ldots, -(k-1), k^2-k, -(k-1), \ldots, -2, -1]$ is based on double moving average and scaled-up by $k^2$ to obviate fractions. Without scaling the primary filter used by the disclosed technique in the case of NPLF 60 Hz and ECG sampling rate 360 Hz has the frequency response shown by dashed line in FIG. 2. To enhance the band-pass effect and to better clear the region near to the spectral origin where the PLI components related to the NPLF and its harmonics appear after the downsampling owing to the "aliasing" phenomenon, the ECG filtering utilizes a second identical filter organized using FIFO buffers z and u according to lines 92, 93 and 106 in Table 1. Without scaling the two serial band-pass PLI filters used by the disclosed technique in the considered case of NPLF and ECG sampling rate have the frequency response shown by solid line in FIG. 2. Another important property of thus realized band-pass PLI filtering is its practically proven insensitiveness to the moderate signal variations within the typical T-waves in the ECG;

Determining the error in LS linear approximation of the recent four differences d of phased with the NPLF ECG samples and storing in the respective buffers e and f the last two approximation errors and their sum as new smoothed error. The derived scaled-up expression for e is given by lines 96-99 of the M-file and uses 64-bit floating point 'double' operations that in the online version of the disclosed technique are replaced by their much faster 'int64' counterparts. The errors e and f increase when the differences d originate from ECG samples comprising sizable random noise, PLI with deviating from the nominal frequency or varying amplitude and fast non-parabolic change (e.g. a sharp QRS-complex) in the pure ECG signal;

Provided that i≥i2, finding out the maximum mf of the smoothed errors f from 50-56 ms ECG around the current output value of the band-pass PLI filters, computing an integer weight for the final LS approximation and storing this weight and its product with the current PLI filtered value p in the respective FIFO buffers w and v of lengths corresponding to 0.4 s. The weights w computed according to line 105 in Table 1 range from 1 to 1000 in a manner depending on the denominator addend da whose experimental adjusting is explained further;

Provided that i≥i3, estimating PLI by weighted LS parabolic approximation realized in lines 112-136 of Table 1 following the widely known analytical approach to such problem. The current sub-series t of downsampled to the NPLF LS weights w is used to compute the quantities D0, D1, D2 and D participating in the final PLI estimate given in the line 136 of the M-file (note that the factor $k^4$ in D counterpoises the aggregate scale-up of the band-pass PLI filters). Weighted PLI values v are downsampled in a vector l used to obtain the rest quantities in the final PLI estimate which at the end is subtracted from the target ECG sample x(nx) that is last in the respective FIFO buffer.

The M-file in Table 1 shows that most computations of the disclosed technique are involved in the determination of the errors e and mainly in the operators for multiplying the elements of vectors t and l by their LS indices that range from −10 to 10 for NPLF 50 Hz and from −12 to 12 for NPLF 60 Hz. To enhance its real-time capacity, in the online version of the technique all expressions K*X, where X is 'int32' or 'int64' variable and K is fixed integer coefficient in the range from 2 to 12, instead by general purpose multiplication are computed utilizing binary arithmetic shift operations, e.g. 11*X is obtained by ((X*2)*2+X)*2+X.

Figure 3:
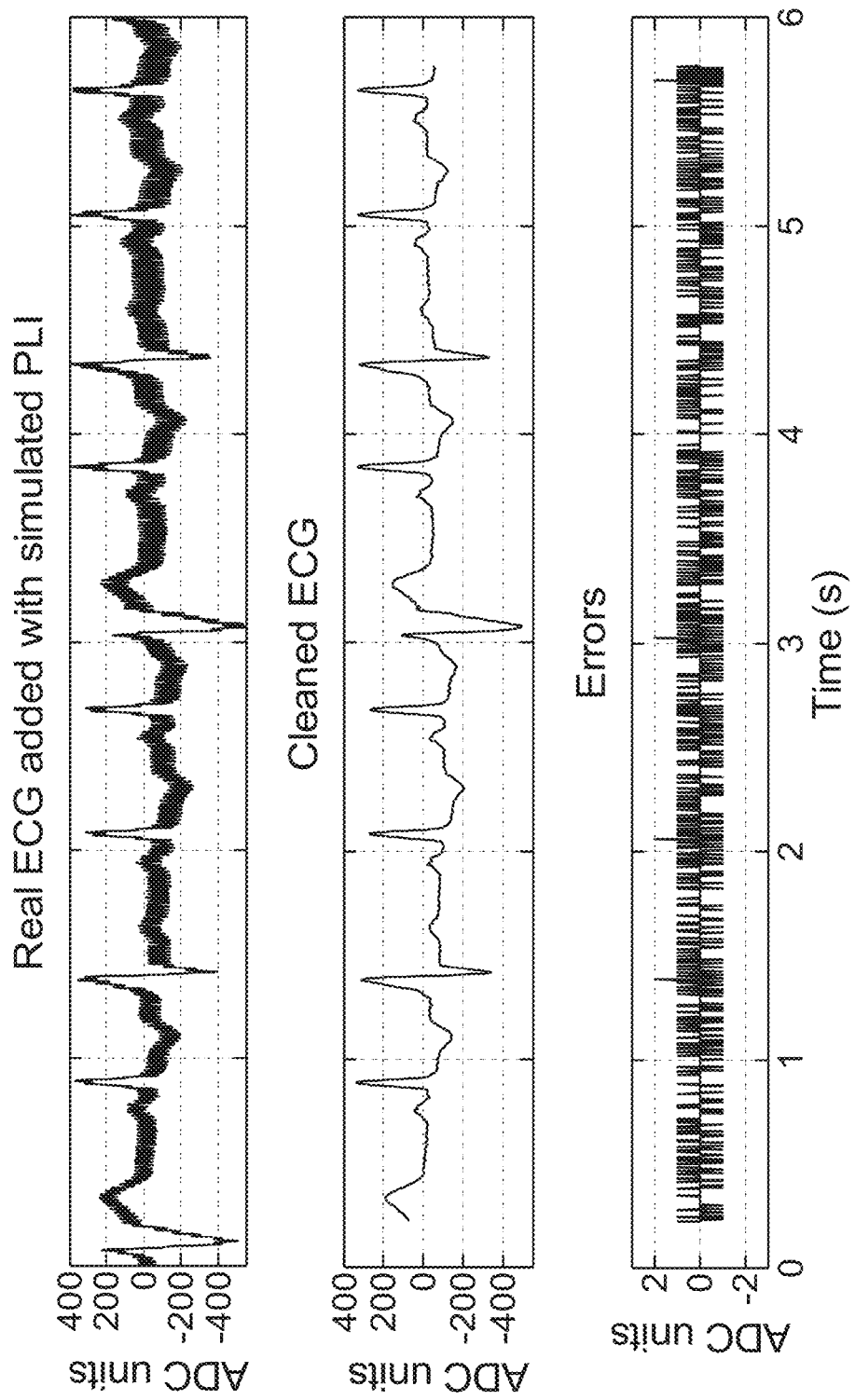
FIG. 3 illustrates a trial of the disclosed technique for removing simulated PLI with deviating from 60 Hz frequency and varying amplitude in a real ECG sampled with 360 Hz.

The disclosed technique for real-time removal of PLI in ECG is tested using various synthesized and real signals. FIG. 3 displays a trial with an apparently clean real ECG record sampled with 360 Hz and 11-bit resolution over a 10 mV range. According to lines 68-71 in Table 1 the original ECG is added with simulated PLI having main component with varying from 50 to 100 ADC units amplitude and deviating from 60.2 to 60.6 Hz frequency and third harmonic of constant amplitude 5 ADC units (note that the correct setting of the endmost PLI frequency is expanded in line 70 and that the simulated PLI values are converted to 'int16'). The processed mixed signal is shown in the top panel of FIG. 3, whose next panel displays the cleaned PLI obtained by the disclosed technique (note its starting interval of about 0.2 s and the same real-time delay on the right side), and the bottom panel in FIG. 3 presents the integer differences between the original and the cleaned ECG which are considered as errors. FIG. 3 demonstrates that the disclosed technique is very accurate—despite that both the real ECG and the simulated PLI are quite complex, the mean absolute error is only 0.3 ADC units.

Figure 4:
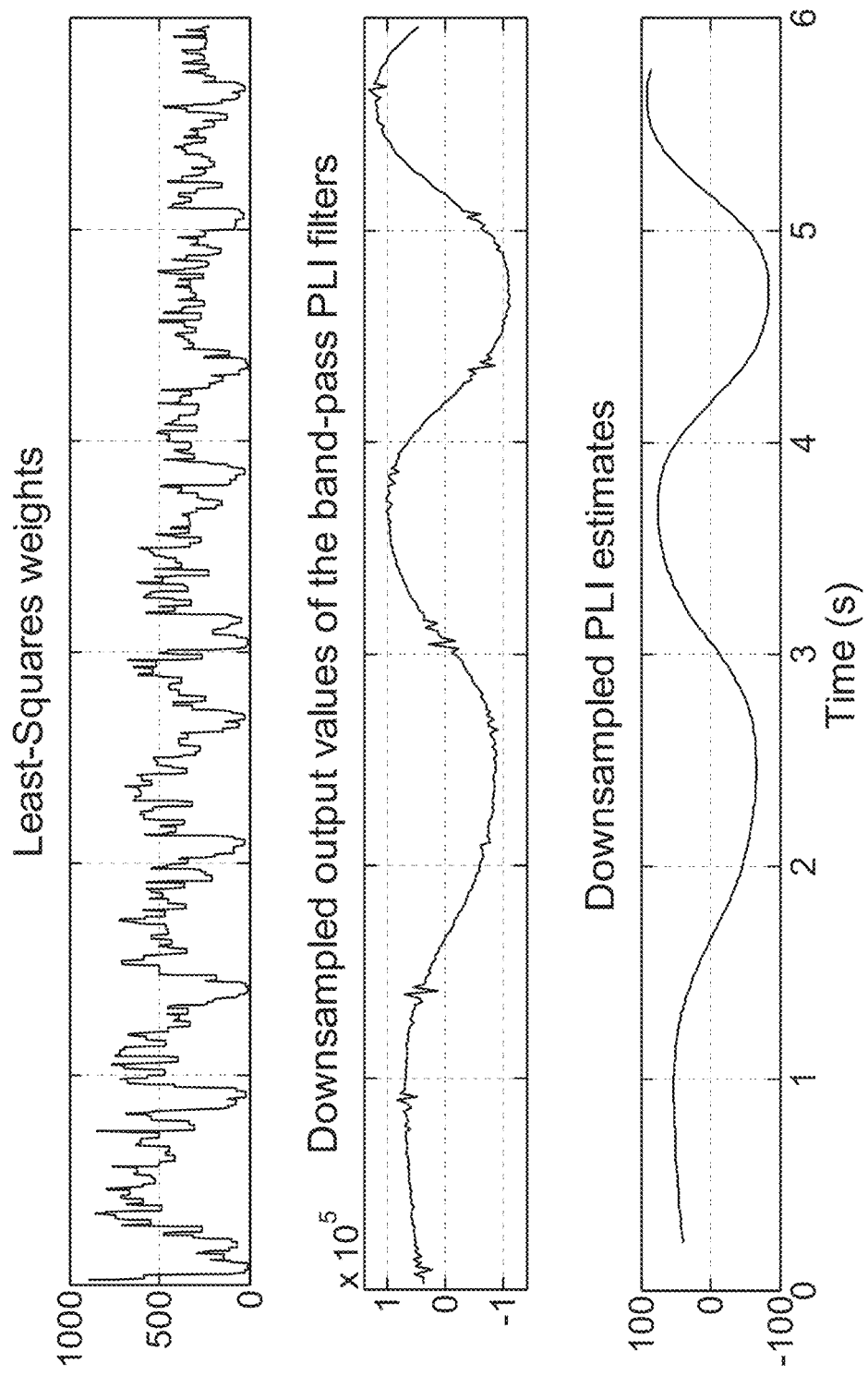
FIG. 4 represents major intermediate results in the example of FIG. 3.
Figure 5:
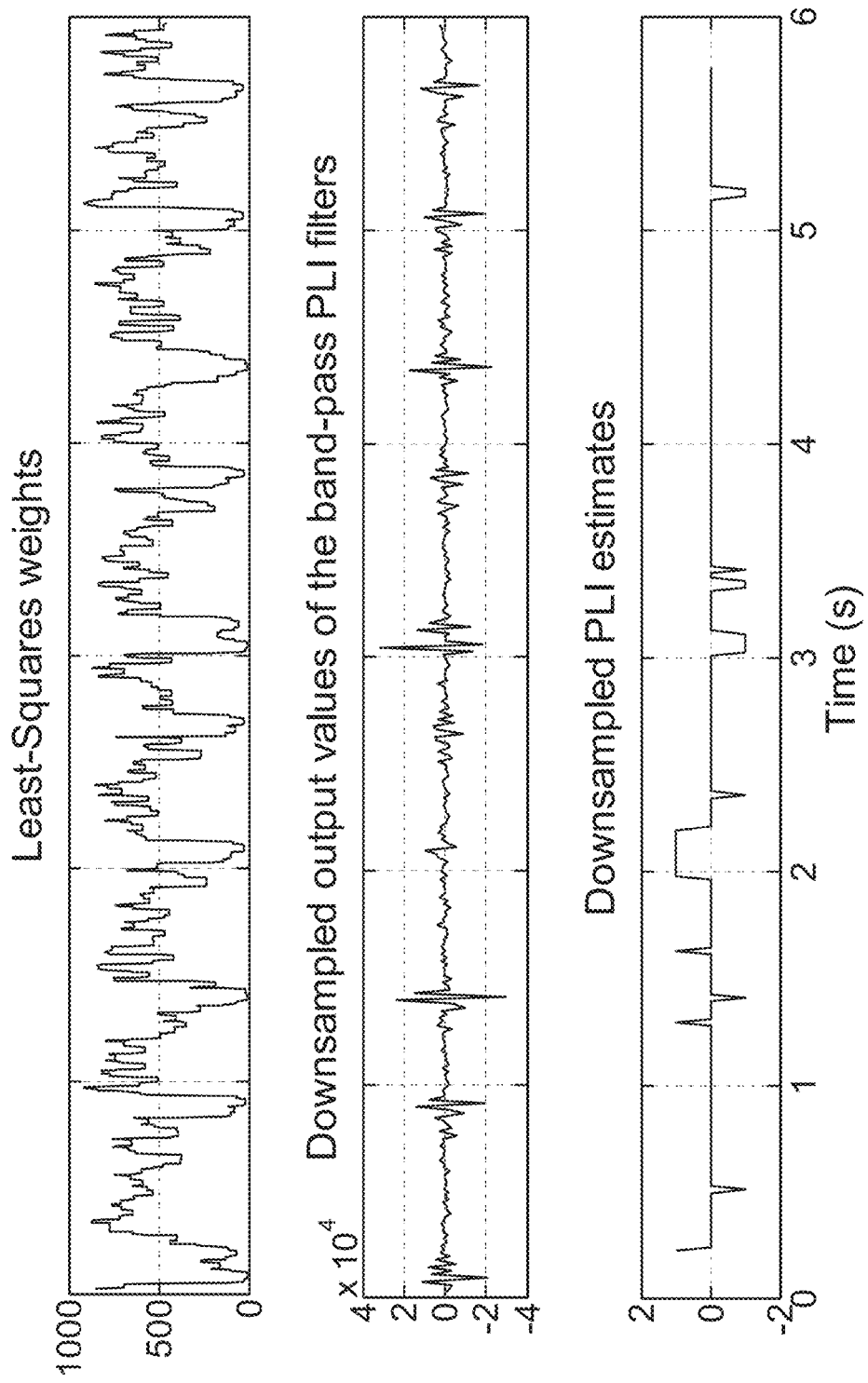
FIG. 5 displays major intermediate results obtained using only the real ECG of FIG. 3.

To better elucidate the operation of the disclosed technique, major intermediate results from the example of FIG. 3 are presented in FIG. 4, and FIG. 5 displays corresponding results obtained treating the real ECG of FIG. 3 without added PLI. Top panels of FIG. 4 and FIG. 5 show how the weights used in the final LS approximation depend on the QRS-complexes and P-waves in the pure ECG signal and on the PLI characteristics. Middle panels presenting one of the six sub-series of downsampled to the NPLF output values of the band-pass PLI filters demonstrate the effects of the "aliasing" phenomenon (FIG. 4), of the filters scaling-up and of the QRS-complexes and P-waves in the ECG that cause appreciable disturbances in the band-pass PLI filtered signal (FIG. 5). Nevertheless owing to the expedient weighting the final LS parabolic approximation yields the displayed in the bottom panels of FIGS. 4 and 5 sub-series of downsampled PLI estimates that accurately quantify the actual PLI in the processed ECG.

Regarding the results of FIG. 5 it should be added that in this PLI-free trial more than 80% of the treated original ECG samples are not altered, whereas the rest are changed by one ADC unit only. Because the preservation of the pure ECG signals is of prime importance, the denominator addend da that regulates the weighting for the final LS approximation is adjusted experimentally using free of PLI real ECG records with low to medium sized random noise. The adjusting purpose is for at least 10 such records with various ECG features and arrays W of LS weights to attain close to 500 median(W) representing the "quiet" ECG epochs. In fact the adjusting of da is quite easy since according to the expression of line 105 in Table 1 w≅500 come from mf≅da whereas lower mf give higher w and vice versa. Therefore median(W) corresponds to median(MF) and hence the parameter da is set close to a rough average of all excepting eventual outlier medians of the arrays MF obtained from the selected ECG records.

Figure 6:
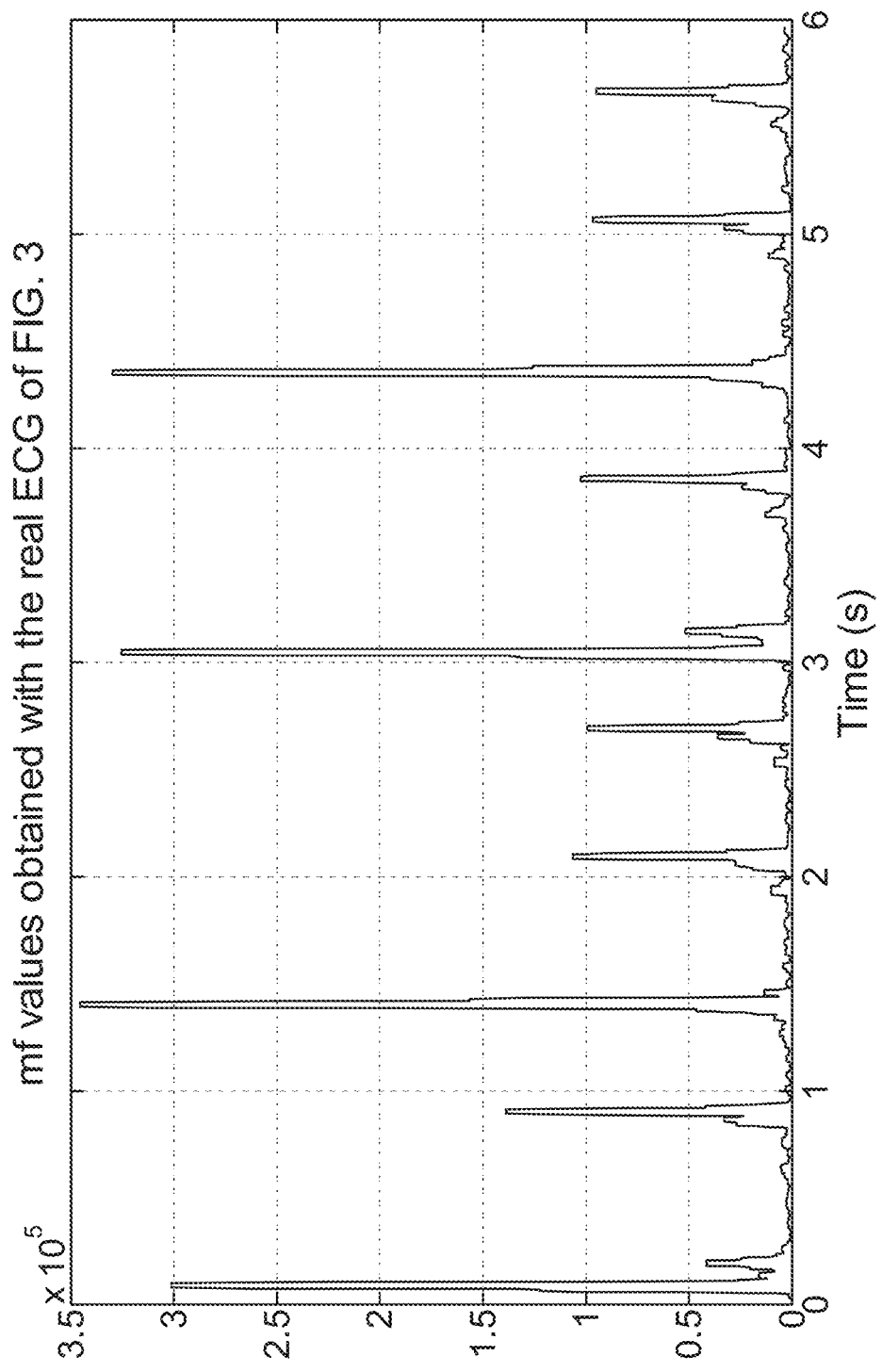
FIG. 6 shows others intermediate results with the real ECG of FIG. 3.

The real ECG of FIG. 3 gives the presented in FIG. 6 mf values with median(MF)=2690 and the respective weights w shown in the top panel of FIG. 5, which are obtained using the experimentally adjusted da=3000, have median(W)=528 representing the LS weights in the "quiet" epochs of the exemplary record taken from a series of about 100 ECG signals that are sampled with 360 Hz and 11-bit resolution over a 10 mV range.

Because recently most ECG devices use 12-bit ADC over 10 mV range, the disclosed technique is also adjusted for this higher resolution expecting some numerical increase of the parameter da. However following the above procedure, the same da=3000 is selected for all the five embodiments of the technique owing to the lower overall level of the inherent random noise in the real ECG records with 12-bit resolution used for adjusting the parameter da.

The disclosed technique is tested using directly or with added simulated PLI more than 400 ECG signals with highly varied characteristics. The tests show that the technique is both accurate and reliable (no failures or wrong results are detected) and indicate that after proper adjustment the disclosed technique is also applicable for real-time removal of PLI in ECG signals with still higher resolution, e.g. 14- or 16-bit over a 10 mV range.

From the above description of the five preferred embodiments, those skilled in the art will not only understand the invention and its advantages, but will also find apparent various changes of the disclosed technique for real-time removal of power line interference in ECG. Therefore it is sought to cover all such modifications as falling within the spirit and scope of the present invention defined by the appended claims.

TABLE 1

| 1 | | |
|---|---|---|
| 2 | clear; | % clear MATLAB workspace |
| 3 | | |
| 4 | % adjusting parameters (in the online version | |
| 5 | % use 'int64' instead of each present 'double') | |
| 6 | | |
| 7 | pf = 60; | % nominal power line frequency (Hz) |
| 8 | sf = 360; | % ECG sampling rate (Hz) |
| 9 | | |
| 10 | if pf == 60 & sf == 240 | |
| 11 | nf = 5; | % number of smoothed errors |
| 12 | ff = 1; | % first smoothed error in use |

TABLE 1-continued

```
13      elseif pf == 60 & sf == 300
14          nf = 8;
15          ff = 1;
16      elseif pf == 60 & sf == 360
17          nf = 10;
18          ff = 2;
19      elseif pf == 50 & sf == 250
20          nf = 7;
21          ff = 2;
22      elseif pf == 50 & sf == 300
23          nf = 9;
24          ff = 3;
25      else return              % inadmissible pf and/or sf
26      end
27
28      % experimentally adjusted parameters
29      % for determination of the LS weights
30
31      da = double(3000);       % denominator addend
32      na = double(1000*da);    % numerator addend
33
34      nfm = nf-1;
35      k = sf/pf;               % ratio k = 4, 5 or 6 of sf and pf
36      km = k-1;
37      kp = k+1;
38      k2 = int32(k^2);         % squared k
39      k4 = double(k^4);
40      i1 = 2*k-1;              % first transitional index
41      i2 = 2*i1-1;             % second transitional index
42      nw = 2*sf/5+1;           % number of stored LS weights
43      nwm = nw-1;
44      i3 = i2+nwm;             % third transitional index
45      nx = i1+sf/5;            % number of stored ECG samples
46      nxm = nx-1;
47      m = pf/5;                % parameter for LS indices
48      ind = int32([-m:m]);     % 2m+1 LS indices
49
50      % initially zeroed FIFO buffers for:
51
52      x = zeros(1,nx,'int16');      % ECG samples
53      d = zeros(1,4,'int32');       % differences of phased
54                                    % with NPLF ECG samples
55      y = zeros(1,k,'int32');       % sums of ECG samples
56      z = zeros(1,kp,'int32');      % filtered ECG samples
57      u = zeros(1,k,'int32');       % sums of filtered samples
58      e = zeros(1,2,'double');      % approximation errors
59      f = zeros(1,nf,'double');     % smoothed errors
60      w = zeros(1,nw,'int16');      % LS weights
61      v = zeros(1,nw,'double');     % weighted PLI values
62
63      % load ECG (or sample ADC in the online version)
64
65      load realecg;            % row vector 'ecg' with real ECG
66      NP = length(ecg);        % number of 16-bit ECG samples
67      ti = (0:NP-1)/sf;        % time instants of ECG samples (s)
68      s = ecg+...              % real ECG with added simulated PLI
69          int16(linspace(50,100,NP).*cos(2*pi*...
70          linspace(pf+0.2,pf+0.2+(0.6-0.2)/2,NP).*ti+1)+ ...
71          5*cos(6*pi*linspace(pf+0.2,pf+0.4,NP).*ti));
72      cs = zeros(1,NP,'int16'); % storage for cleaned ECG
73      % (in the online version s and cs are single non-
74      % indexed 16-bit variables)
75
76      % processing of each consecutive ECG sample
77
78      i = 0;                   % running index
79      while i < NP  % don't use this control in the online version
80          i = i+1;
81          x(nx:-1:2) = x(nxm:-1:1);   % shift stored ECG samples
82          x(1) = s(i);                % store current ECG sample
83          d(4:-1:2) = d(3:-1:1);      % shift differences
84          d(1) = int32(x(1))-int32(x(kp)); % difference of phased
85                                           % with NPLF ECG samples
86          y(k:-1:2) = y(km:-1:1);
87          y(1) = y(2)+d(1);           % recursive sum of last k samples
88          if i >= i1
89              z(kp:-1:2) = z(k:-1:1); % shift filtered ECG samples
90              z(1) = k2*int32(x(k))-sum(y,'native');  % scaled
91                                      % by k2 band-pass PLI filter
92              u(k:-1:2) = u(km:-1:1);
93              u(1) = u(2)+z(1)-z(kp); % recursive sum of last k
94                                      % filtered ECG samples
95              e(2) = e(1);            % shift approximation errors
96              e(1) = double(3*d(1)-4*d(2)-d(3)+2*d(4))^2+...
97                     double(4*d(1)-7*d(2)+2*d(3)+d(4))^2+...
98                     double(d(1)+2*d(2)-7*d(3)+4*d(4))^2+...
99                     double(2*d(1)-d(2)-4*d(3)+3*d(4))^2;
100             f(nf:-1:2) = f(nfm:-1:1);
101             f(1) = e(1)-e(2);  % smooth by adding last 2 errors
102             if i >= i2
103                 mf = max(f(ff:nf));  % maximum smoothed error
104                 w(nw:-1:2) = w(nwm:-1:1);
105                 w(1) = int16((mf+na)/(mf+da)); % 16-bit LS weight
106                 p = k2*z(k)-sum(u:'native');   % second scaled
107                                     % by k2 band-pass PLI filter
108                 v(nw:-1:2) = v(nwm:-1:1);
109                 v(1) = double(w(1))*p; % 64-bit weighted PLI value
110                 if i >= i3
111     % in the online version put 'i = i3;' here to prevent overflow
112                     t = int32(w(1:k:nw));   % pick out 2m+1
113                                     % downsampled to NPLF LS weights
114                     p0 = sum(t);
115                     t = t.*ind; % multiply each weight by its LS index
116                     p1 = sum(t);
117                     t = t.*ind;     % multiply again by LS indices
118                     p2 = sum(t);
119                     t = t.*ind;     % multiply again by LS indices
120                     p3 = sum(t);
121                     t = t.*ind;     % multiply again by LS indices
122                     p4 = sum(t);
123                     D0 = p2*p4-p3^2;
124                     D1 = p1*p4-p2*p3;
125                     D2 = p1*p3-p2^2;
126                     D = k4*(p0*D0-p1*D1+p2*D2); % the factor k4
127                                     % counterpoises filters scale-up
128                     I = v(1:k:nw);  % pick out 2m+1 downsampled
129                                     % to NPLF weighted PLI values
130                     p0 = sum(I);
131                     I = I.*double(ind);   % multiply each weighted
132                                     % PLI value by its LS index
133                     p1 = sum(I);
134                     I = I.*double(ind); % multiply again by LS indices
135                     p2 = sum(I);
136                     cs(i-nxm)=x(nx)-int16((p0*D0-p1*D1+p2*D2)/D);
137     % subtract PLI estimate and store the result in due place
138                 end
139             end
140         end
141     end
142
```

REFERENCES CITED

U.S. PATENT DOCUMENTS

| | | | |
|---|---|---|---|
| 5,687,735 | November 1997 | Forbes et al. | 128/696 |
| 6,216,031 | April 2001 | Findeis et al. | 600/509 |
| 6,351,664 | February 2002 | Brodnick | 600/509 |
| 7,286,983 | October 2007 | Li et al. | 704/226 |
| 7,894,885 | February 2011 | Bartal et al. | 600/509 |

Other Publications

I. P. Mitov, "A method for reduction of power line interference in the ECG", *Medical Engineering & Physics*, vol. 26, No. 10, December 2004, pp. 879-887.

What is claimed is:

1. A technique for real-time removal of power line interference (PLI) in electrocardiographic (ECG) devices with sampling rate sf set equal to an integer multiple of the nominal power line frequency (NPLF, given by pf=60 or 50

Hz) in a range from 240 Hz to 6*pf Hz, the technique comprising the following steps performed in each of said ECG devices after every sampling:

(a) storing into a part of the ECG device memory a current sample obtained by analog-to-digital conversion of the treated ECG signal as x(1) in a First-In-First-Out (FIFO) buffer of 16-bit integers x(j), where j=1, . . . ,nx, nx=2*k−1+sf/5 and k=sf/pf is 4, 5 or 6, computing a 32-bit difference d(.)=x(1)−x(1+k) of phased with the NPLF ECG samples x(1) and x(1+k) for said k=4, 5 or 6 in said FIFO buffer x(j) and storing said d(.) as d(1) in a FIFO buffer of 32-bit integers d(j) with j=1 , . . . ,4;

(b) filtering ECG samples x(1), . . . ,x(4*k−3) with said k=4, 5 or 6 in said FIFO buffer x(j) by a series of two identical band-pass PLI filters that are based on double moving average and have scaled-up to obviate fractional numbers impulse responses [−1, −2, . . . , −(k−1), $k^2$−k, −(k−1), . . . , −2, −1] for said k=4, 5 or 6;

(c) determining a 64-bit integer e(.)=(3*d(1)−4*d(2)−d(3)+2*d(4))²+(4*d(1)−7*d(2) +2*d(3)+d(4))²+(d(1)+2*d(2)−7*d(3)+4*d(4))²+(2*d(1)−d(2)−4*d(3)+3*d(4))² in Least-Squares (LS) linear approximation of said four 32-bit differences d(j) in said FIFO buffer, storing said e(.) as e(1) in a FIFO buffer of two 64-bit integers [e(1), e(2)], and storing f(.)=e(1)+e(2) as a new smoothed error f(1) in a FIFO buffer f(j) with j=1, . . . ,nf, where nf and a first index for use ff are pre-adjusted to dependent on said pf and sf values specified below;

(d) determining a maximum mf of smoothed errors f(ff), . . . ,f(nj) in said FIFO buffer f(j), computing a ranged from 1 to 1000 integer weight w(.)=(mf+1000*da)/(mf+da), where da is parameter that for said ECG devices with analog-to-digital converters of 11- or 12-bit resolution over a 10 mV range is experimentally adjusted to da=3000, and storing said w(.) and its 64-bit integer product v(.) with a current output value of said band-pass PLI filters as w(1) and respectively v(1) in two FIFO buffers w(j) and v(j) with j=1, . . . ,nw, nw=2*sf/5+1 and lengths corresponding to 0.4 s;

(e) estimating PLI by weighted LS parabolic approximating that uses a pair of current sub-series [w(1), w(k+1), . . . , w(nw)] and [v(1), v(k+1), . . . , v(nw)] for said k=4, 5 or 6 that at said pf=60 or 50 Hz have LS indices [−m, . . . ,m] with m=pf/5 and subsume each 2*m+1 of downsampled to the NPLF weights w(j) and products v(j) in said FIFO buffers, and subtracting thus obtained PLI estimate from ECG sample x(nx) that is last in said FIFO buffer x(j), thereby producing a cleaned of power line interference electrocardiogram for usable printing or displaying by said ECG devices.

2. A technique as set forth in claim 1, comprising real-time removing of PLI in each of said ECG devices using solely integer arithmetic operations performed by an ECG device processor on said 16-, 32- and 64-bit numbers.

3. A technique as set forth in claim 2, comprising pre-adjusting for real-time removing PLI of nominal frequency 60 Hz in said ECG devices with sampling rate 240 Hz (in that case said ff and nf are set ff=1, nf=5), 300 Hz (in that case said ff and nf are set ff=1, nf=8) or 360 Hz (in that case said ff and nf are set ff=2, nf=10), and for real-time removing PLI of nominal frequency 50 Hz in said ECG devices with sampling rate 250 Hz (in that case said ff and nf are set ff=2, nf=7) or 300 Hz (in that case said ff and nf are set ff=3, nf=9).

* * * * *